United States Patent [19]

Evenstad et al.

[11] 4,347,237

[45] Aug. 31, 1982

[54] LOWER FATTY ACID GLYCERIDE HIGH-HLB LUBRICATING SUPPOSITORY AND METHOD FOR MAKING AND USING THE SAME

[76] Inventors: Kenneth L. Evenstad, 16235 Holdridge Rd., Wayzata, Minn. 55391; Hiep Nguyen, 18605 33rd Ave. North, Plymouth, Minn. 55447

[21] Appl. No.: 239,882

[22] Filed: Mar. 2, 1981

[51] Int. Cl.$^3$ .............................................. A61K 9/02
[52] U.S. Cl. ..................................... 424/78; 424/358; 424/365; 424/DIG. 14; 424/DIG. 15
[58] Field of Search ............... 424/DIG. 14, DIG. 15, 424/358, 365, 78

[56] References Cited

U.S. PATENT DOCUMENTS

| | | | |
|---|---|---|---|
| 2,469,618 | 5/1949 | Ward et al. | 424/365 |
| 2,538,127 | 1/1951 | Saunders et al. | 424/365 |
| 2,889,250 | 6/1959 | Mende et al. | 424/365 |
| 2,890,983 | 6/1959 | Monot | 424/365 |
| 2,975,099 | 3/1961 | Goyan et al. | 424/181 |
| 2,988,484 | 6/1961 | Barsky et al. | 424/365 |
| 3,756,238 | 9/1973 | Hanke | 128/270 |
| 3,776,001 | 12/1973 | Hanke | 424/32 |
| 3,815,600 | 6/1974 | Groves | 128/271 |
| 3,884,233 | 5/1975 | Summey | 128/263 |
| 3,886,940 | 6/1975 | Hunger | 128/271 |
| 4,026,292 | 5/1977 | Hutchins et al. | 128/285 |
| 4,140,756 | 2/1979 | Gallian | 424/21 |
| 4,232,003 | 11/1980 | Posthuma | 424/DIG. 14 |
| 4,277,461 | 7/1981 | Lucker et al. | 424/DIG. 15 |

FOREIGN PATENT DOCUMENTS 1396613  4/1964  France ............................... 424/365

OTHER PUBLICATIONS

WO80/00410 Published Mar. 20, 1980, Van Cleave, Anhydrous Multipurpose Moisturizing Composition, 27 pp.
Lachman et al., The Theory and Practice Of Industrial Pharmacy 2nd Ed., Lea & Febiger, Phila, Pa., 1976, pp. 245–269, 238–244, 189–201, 206, 215–229.
Kata et al., Chem. Abstr. 71 #128667f (1969), Drug Release from Suppositories As A Function Of The HLB (Hydrophile–Lipophile Balance) Value.
Turakka et al., Chem. Abstr. 82 #129248j (1975), Effect Of The HLB (Hydrophile–Lipophile Balance) Value Of The Surface Active Agent On The Rate Of Release Of Drugs From Suppositories.
Gross et al., J. A. Ph. A. Sci. Ed., vol. XLII No. 2, Feb. 1953, 90–95, A Study Of Suppository Bases I. Review of Literature.
Ward, J. Am. Pharm. Assoc. of Sci. Ed., 39: 265–266, (1950).

*Primary Examiner*—Shep K. Rose
*Attorney, Agent, or Firm*—Merchant, Gould, Smith, Edell, Welter & Schmidt

[57] ABSTRACT

The disclosed lubricating suppository is formulated to have properties advantageous for coital use, including extraordinary water washability. The ingredients and phase relationships of the suppository composition provide a high degree of compatibility with water and with naturally-occurring vaginal moisture. The suppository composition contains a glyceride lubricant and can be lubricious with or without the presence of moisture. The suppository, which is solid at room temperature but melts in a short time at body temperature, is made by dissolving, for example, 10–30 parts by weight of high-HLB (e.g. >14) nonionic surfactant in 50–70 parts by weight of a molten, water-soluble polyoxyethylene glycol component and by dispersing or emulsifying 10–20 parts by weight of the glyceride (e.g. a triglyceride of $C_6$–$C_{18}$ aliphatic carboxylic acids) included in the composition. In use, the suppository can be inserted prior to coitus and permitted to melt to a liquid, which is lubricious even in the absence of moisture, but still has the aforementioned extraordinary water washability.

12 Claims, No Drawings

LOWER FATTY ACID GLYCERIDE HIGH-HLB LUBRICATING SUPPOSITORY AND METHOD FOR MAKING AND USING THE SAME

This invention relates to a lubricant in the form of a suppository, which lubricant is designed specifically for the human vagina. An aspect of this invention relates to a pre-coital lubricant in suppository form. Still another aspect of this invention relates to a method for lubricating the human vagina by insertion of a solid suppository which melts to form a lubricant at human body temperature. Still another aspect of this invention relates to a method for making a lubricating suppository from a plurality of generally solid materials, at least one of which is lubricious at normal ambient temperatures.

DESCRIPTION OF THE PRIOR ART

A variety of materials have been suggested as lubricants for human body canals, particularly the vaginal and anal canals. The requirements of such lubricants vary depending upon the reason for lubricating the inside surfaces of the canal. Prior to or during coitus, the human body itself provides some natural lubrication. However, there is a well-established market for materials which supplement the function of the natural lubricant.

Theoretically, any lubricious material which is not harmful to skin could be a pre-coital lubricant, and petroleum jelly, mineral or triglyceride oils, and similar biologically inert, oleophilic materials have been used for this purpose. Like any oleophilic materials, however, they are capable of staining fabric, are relatively incompatible with natural vaginal moisture, and may resist removal from the skin or the interior of the vaginal canal when plain water rinses are used. The pharmaceutical, cosmetic, and personal care industries have accordingly made an effort to formulate lubricants which are better suited for pre-coital use and other vaginal canal lubricating purposes. A composition known as "K Y Jelly" is an example of a sterile, general purpose lubricant with label instructions for use as a lubricant in obstetrical and gynecological procedures and to aid in the insertion of thermometers and other instruments into the vagina or rectum. "Ortho Personal Lubricant", on the other hand, is an example of a composition labelled for use specifically for sexual intercourse. Nevertheless, the latter product is somewhat similar in its composition to the sterile, general purpose jelly. Both products contain a major amount of water combined with a cellulose derivative and are packaged in collapsible tubes. The predominantly aqueous nature of these products can provide advantages over oleaginous materials for the reasons already indicated, but because the water portion of both of these formulations appears to play an important role in making the product lubricious, upon evaporation the lubricity may be lost. Such evaporation can occur even during coitus.

When insertion of any material into a human body canal (particularly the vagina or anus) is desirable, suppositories have advantages and are often preferred by patients, doctors, and other users. The suppository art is a highly developed one, particularly with respect to suppositories which provide a matrix for releasing some medicament. Such suppositories can be made lubricious; see, for example, U.S. Pat. No. 3,776,001 (Hanke), issued Dec. 4, 1973. Medicators, tampons, and the like have also been made lubricious, at least on their surfaces. The following references are believed to be reasonably representative of this art.

| U.S. Pat. No. | Issue Date | Patentee |
| --- | --- | --- |
| 3,756,238 | September 4, 1973 | Hanke |
| 3,815,600 | June 11, 1974 | Groves |
| 3,884,233 | May 20, 1975 | Summey |
| 3,886,940 | June 3, 1975 | Hunger |
| 4,026,292 | May 31, 1977 | Hutchins et al |
| 4,140,756 | February 20, 1979 | Gallian |

SUMMARY OF THE INVENTION

It has now been found that a pre-coital lubricant can be formulated such that it is suitable for formation into suppositories and is not dependent upon a high level of water content or moisture to be lubricious, but yet is water-washable to a far greater degree than any of the common oleaginous lubricants. Indeed, lubricants of this invention have a high level of compatibility with plain water and can easily be solvated or uniformly distributed (dissolved and/or dispersed and/or suspended) in water. Suppositories of this invention are solid at normal ambient temperatures but melt at human body temperature to form a substantially homogeneous liquid having the appearance of a single liquid phase, even though a glyceride of an aliphatic carboxylic acid is distributed through this homogeneous liquid. In either the liquid or solid state, suppositories of this invention comprise:

(a) a continuous phase comprising a polyoxyalkylene polyol component consisting essentially of polyethylene glycols having a molecular weight within the range of 400 to 5,000, so that this component will have a melting range low enough for the purposes of this invention;

(b) about 10–60 parts, per 100 parts by weight of the aforementioned polyol component (and typically 10–30% by weight of the suppository), of a nonionic surfactant having an HLB value greater than 12 (typically this surfactant dissolves in the polyol component); and (c) about 10–40 parts per hundred, based on the weight of the polyol component, of a glyceride (preferably a triglyceride) of an aliphatic carboxylic acid, which glyceride is uniformly distributed throughout the continuous phase with the aid of the nonionic surfactant.

The human vagina can be pre-coitally lubricated with a suppository of this invention by inserting the solid suppository and permitting it to melt within the vaginal canal prior to coitus. The melting is generally complete within a very few minutes. If desired, the insertion can take place up to a few hours before coitus.

Suppositories of this invention are made by melting the polyethylene glycols at a moderately elevated temperature, thereby obtaining a homogeneous melt. The preferred nonionic surfactant (including surfactant combinations) can be dissolved in the melt. The resulting hot mixture is a suitable medium for distributing the glyceride, which is the primary lubricating substance. When a suitable blend has been formed, it can be cast into the form of suppositories using molds or a suppository packaging material that serves as both mold and package.

DETAILED DESCRIPTION

As will be apparent from the foregoing brief summary, this invention is tailored specifically to the requirements of pre-coital lubrication, although suppositories of this invention may incidentally facilitate insertion of medical instruments or the like into human body canals. For coital lubrication, compatibility with water or moisture is desirable not only to provide water washability, but also to facilitate combination with natural vaginal moisture and uniform spreading throughout the surfaces of the vaginal canal. A relatively low viscosity in the molten state also improves the pre-coital lubricating function of this invention. Such low viscosity may have one drawback, however: the lubricant can easily pass from the vaginal canal onto clothing or other fabric. To overcome this drawback, it has been found that an extremely high level of water compatibility can be provided without losing any of the other advantages of this invention. A solid residue or stain (e.g. on fabric) from such leakage can be removed with plain water because of the extraordinarily high level of dispersion of the oleaginous phase or phases of the lubricant and the compatibility of the nonionic surfactants with the polyoxyethylene glycol base. Compositions of this invention need not and preferably do not contain any solid material which will not readily disperse or become suspended in water. Even the cellulosic materials of the prior art are more difficult to suspend or disperse in water than compositions of this invention. The polyoxyalkylene polyol component, since it consists essentially of polyethylene glycols is essentially soluble in water. The nonionic surfactant component is essentially soluble in the polyethylene glycols, thereby simplifying the phase relationship between the glycols and the glyceride lubricant. The concentration of nonionic surfactant is high enough to insure that the glyceride will be well emulsified and can be re-emulsified if a spot or stain on fabric results from the use of this invention.

Even in the absence of natural vaginal moisture, a fully or partially melted suppository or vaginal insert of this invention has lubricating properties. The unique combination of ingredients of this invention further allows the melted lubricating substance to become miscible with the vaginal moisture present even in small amounts. As the insert or suppository melts and mixes with any vaginal moisture, it spreads readily throughout the vagina. In addition, the lubricity of the invention is not reduced due to evaporation of moisture during coitus.

In addition to the glycol, glyceride lubricant, and surfactant components of a composition of this invention, the composition can be further modified with a lower aliphatic monomeric hydrophilic polyol which will dissolve in the glycol phase. A preferred monomeric polyol is glycerin. Pigments, fillers, extenders, preservatives, and antioxidants can also be included in the composition, but it is ordinarily preferred to avoid the use of any filler, extender, or pigment which will leave a visible solid residue. For antioxidant or preservative effects, various FDA-approved compounds are suitable, including the conventional alkylated hydroxy aromatic compounds such as BHT (butylated hydroxytoluene) or BHA (butylated hydroxyanisole).

Typical compositions of this invention will now be described in greater detail.

THE CONTINUOUS PHASE

The major amount of the continuous phase comprises one or more (preferably a blend) of polyoxyethylene or polyethylene glycols. These glycols contain an oxyethylene chain with an extraordinary compatibility with water and with a hydroscopicity of at least 0.1%, preferably at least 1% of glycerin. Because these polyethylene glycols make up such a large proportion of the lubricating suppository, it is preferred that a single such glycol (if used alone) or any combination of such glycols be solid at normal ambient temperatures (20°–25° C.) and preferably at moderately elevated temperatures which may inadvertantly be reached during storage, e.g. 30° or 35° C. On the other hand, it is desirable that the glycol component be capable of melting at temperatures close to human body temperature (e.g. 37° C.). The melting point of the glycol component can of course be depressed by blending into it compatible liquids or low-melting solids. Nevertheless, it is preferable that, in the absence of such liquids or low-melting solids, the glycol component have a melting point or melting range low enough to insure the formation of a clear molten liquid at less than about 75° C., more preferably at less than about 55° or 60° C. Among the low-melting solids and liquids which can provide the aforementioned melting point depressant effect are low molecular weight polyoxyethylene glycols which are available in molecular weights well below 1,000 (equivalent weights well below 500). It is preferred however to keep the molecular weight of the lowest-melting glycol above about 400. A polyethylene glycol having an average molecular weight of about 500 could be a solid at 20° C. but may have the consistency of low-melting petrolatum.

Polyoxyethylene glycols are available in molecular weights above 1,000,000, but most of the molecular weight range above 5,000 is of limited utility in the context of this invention because of the relatively high melting points or solidification ranges of such materials. The optimum average molecular weight range for glycols useful in this invention is above about 900 and below about 2,000, thereby assuring a solidification range below 60° C. A blend of such glycols within this molecular weight range will generally begin to melt at temperatures no higher than about 50° C. With "fine tuning" of the blend, it can be formulated to begin to melt at 36°–38° or 39° C., which is approximately the ideal melting range, absent any melting point depressant other than a low molecular weight polyoxyethylene glycol. With a melting point depressant, this range can be extended to 40° C. and higher, as explained previously. It is desirable in any event that the glycol component begin to melt at 36°–38° C. within a few minutes.

A particularly effective way to provide the water-washability of lubricating compositions of this invention is to insure that the glyceride (e.g. the glyceryl trialkanoate) is well distributed with a surfactant component which is compatible with the polyethylene glycols in the continuous phase and, perhaps equally important, that these glycols have a measurable degree of water solubility, e.g. more than 10% by weight. A remarkable feature of the polyethylene glycols is that even relatively high polymers of ethylene oxide have water solubility. At relatively low molecular weights, these hydroxy-terminated polymers will dissolve to the extent of about 70% by weight (or more) in water. As the molecular weight increases into the thousands, the water solubility declines but not drastically. Polyoxyethylene glycols used in this invention, either individually or in combination, typically have a water solubility in excess of 50% on a weight/weight basis. For this reason, mixtures of oxyethylene polymers with oxypropylene or tetramethyleneoxy polymers are not preferred. Among nonionic polymers, it is difficult to improve upon the water solubility of the oxyethylene (i.e. ethylene oxide) polymers, and certainly the water compatibility of propylene oxide or other oxyalkylene polymers is meager in comparison to the polyoxyethylenes. In short, the oxyalkylene chains obtained from two-carbon oxyalkylene units are unique among this class of structures, particularly in terms of their compatibility with water. Absent modification with pendant or recurring oxyethylene units, other hydrophilic solids such as cellulose also lack this extraordinarily high degree of water compatibility. Relatively hydrophobic or oleophilic compounds which may detract from the water compatibility of the glycol component of this invention are preferably excluded from this component. With the exception of very minor amounts of antioxidants, preservatives, or the like, it will ordinarily be the case that the least hydrophilic ingredient of a composition of this invention will be the glyceride, which is substantially insoluble in water.

In typical suppository compositions of this invention, 50–70% by weight of the composition is made up of this glycol component. The total composition contains a nonionic surfactant component which can be uniformly distributed (dissolved, dispersed, or suspended) through the continuous phase. It is ordinarily preferred that this surfactant component be sufficiently compatible with the continuous phase to form a part of it, thereby simplifying the phase relationships within the composition. It is also preferred that the surfactant have a significant degree of compatibility with water, which can be provided by selecting surfactant compounds or compositions having an HLB value greater than 12, more preferably greater than 14. (The HLB value is the hydrophile-lipophile balance and is determined in accordance with well-known procedures published in the scientific and trade literature; HLB values below 9 are considered generally lipophilic, values of 9–11 are considered intermediate or borderline, and values above 12 are clearly hydrophilic.) Although HLB values of 20 or 30 or more have been reported, it is generally unnecessary to use nonionic surfactants having values significantly above 18. When a combination of surfactants is used (as is particularly preferred in this invention), the overall HLB value can be determined on a weighted-average basis, as is conventional in the detergent art. Some nonionic emulsifiers and other surfactants will actually dissolve in molten polyoxyethylene glycols, foremost among these surfactants being those containing oxyethylene chains such as the poly(oxyethylene) polyol esters, poly(oxyethylene) polyol ethers, and mixtures of these esters and ethers. Some of these compounds, such as polyoxyethylene(20) sorbitan mono-oleate are also water soluble. Several series of polyoxyethylene ethers of higher aliphatic alcohols are commercially available, as are the polyoxyethylene derivatives of higher aliphatic carboxylic acids, e.g. the polyoxyethylene polyol alkanoates. Unsaturated aliphatic carboxylic acids and alcohols can also be used to form the desired polyoxyethylene derivatives. A significant degree of higher aliphatic character can be obtained with acids and alcohols containing at least 6 carbons, preferably at least 10 carbons. At $C_{28}$ and higher, the aliphatic character may become excessive and may even be somewhat excessive at $C_{20}$ or $C_{22}$. Relatively hydrophilic nuclei such as sorbitan and other lower aliphatic monomeric polyols can help to counterbalance the aliphatic character of carbon chains in the $C_{12}$–$C_{20}$ range. An example of a thus-balanced compound is polyoxyethylene (20) sorbitan mono-oleate.

There can be distinct advantages in adding a lower aliphatic monomeric hydrophilic polyol to the continuous phase. Glycerin, for example, is of interest because of its extraordinary affinity for water—about 10–100 times as much hygroscopicity as the preferred polyoxyethylene glycols. Glycerin, in fact, is commonly used as a humectant as well as a solvent, a plasticizer, and an emollient. It is a common ingredient of anal suppositories and is considered safe and effective for a variety of medical uses. (Surfactants generally used in this invention are also considered to be safe materials, the particularly preferred ones having been cleared for food or drug use.) Although glycerin is an optional ingredient in the suppositories of this invention, it is ordinarily preferred to include about 5 to about 20% by weight of this compound, based on the total weight of the suppository composition.

THE EMULSIFIED PHASE

The most important ingredient of the phase which is emulsified in the continuous phase is a lubricitous glyceride, preferably a triglyceride generally considered to be safe and effective for lubricating or plasticizing human skin. The glyceryl lower alkanoates such as triacetin and tributyrin tend to be high boiling liquids which may have plasticizing properties but are less effective as lubricants as compared to triglycerides of the aliphatic carboxylic acids having 6 or more carbon atoms. Some of the most preferred lubricants for skin are of coconut origin and contain triglycerides of $C_6$ through $C_{18}$ carboxylic acids, particularly the saturated aliphatic acids (e.g. capric, caprylic, lauric, palmitic, and stearic acids). These triglycerides can be fractionated to shift the content toward either the $C_6$–$C_{12}$ triglycerides or the $C_{12}$–$C_{18}$ triglycerides, as may be desired. Unfortunately, all of these triglycerides are substantially insoluble in water. Even glyceryl tributyrate (the $C_4$ analog of the coconut-origin triglycerides) is reported to have a solubility in water of only 0.01%. However, the highly effective emulsifier or surfactant component of this invention provides excellent water washability and the prospect of virtually total removal of any triglyceride residue from clothing or other fabric with an essentially plain water rinse. In addition, this emulsifier system helps to provide a clear, apparently homogeneous melt within and above the melting range of the suppository of this invention. Although this invention is not bound by any theory, it is believed that the triglyceride is extremely well dispersed in the composition to the point where the composition approaches the nature of a true solution.

METHOD OF MANUFACTURE

The oxyethylene glycols are normally the first ingredients charged to a heated mixer since they normally make up the major amount of the suppository composition. The temperature within the mixer is maintained at a sufficiently high level to keep the glycols in the molten state without approaching the flash point of any component of the composition. Ordinarily, it is not necessary to exceed a temperature of about 75° C. in the mixer. The glycols form a clear melt, to which the nonionic surfactant system can be added and, preferably, dissolved with stirring. The glyceride is also added under constant stirring, and 15–20 minutes will typically be a sufficient period of agitation to thoroughly disperse or suspend this component. The result will be a uniform distribution of all components of the composition. The glycerin or other hydrophilic polyol can be added to the composition at any suitable stage during manufacture.

The heated mass can be poured from the mixer into molds, demolded, and then individually wrapped in foil/laminate packaging material. Cooling of the mold is particularly desired for the purpose of obtaining rapid and complete solidification of the portion of molten material which has been poured into the mold. Alternatively, the heated mass can be cast into a preformed suppository packaging material that serves as both mold and package.

The preferred method of use is to insert the suppository into the vagina at least about 5 minutes prior to sexual intercourse. If this procedure is not convenient, the suppository can be inserted as much as an hour or two before intercourse, and a sufficient amount of liquid lubricant will still be present in the vaginal canal when intercourse is commenced. After thorough melting of the suppository, leakage of the molten lubricant from the vaginal canal will not vitiate the effectiveness of this invention, because of the compatibility of the triglyceride with natural lubricants, the ease of blending of the lubricant with natural moisture which may be present, the spreading of the lubricant throughout the canal, and the effectiveness of very small residual amounts of the lubricant.

The invention is illustrated in more detail in the following non-limiting Example.

EXAMPLE

A solid suppository was cast from the following formulation.

| Ingredient | Parts by Weight |
| --- | --- |
| Polyethylene glycol, average molecular weight 1300–1600, solidifying range 40–50° C., soft, white waxy solid, solubility in water at 20° C., approximately 70% (weight/weight), pH of a 5% aqueous solution about 6.5 (CARBOWAX ® 1540) | 25 |
| Polyethylene glycol, average molecular weight 950–1050, solidifying range 35–40° C., solubility in water at 20° C. about 70% on a weight/weight basis (CARBOWAX ® 1000) | 25 |
| Glycerin | 10 |
| Polyoxyethylene (23) lauryl ether (BRIJ ® 35) | 10 |
| Polyoxyethylene (20) sorbitan mono-oleate (TWEEN ® 80) | 5* |
| Polyoxyethylene (40) stearate ("MYRJ" 52-5 [trademark]) | 5 |
| Fractionated triglyceride of coconut origin (caprylic/capric triglyceride, "NEOBEE | 20 |

-continued

| Ingredient | Parts by Weight |
| --- | --- |
| M-5" [trademark]) | |

*Alternatively, can be replaced with more BRIJ or MYRJ.

The HLB value of the polyoxyethylene lauryl ether and the polyoxyethylene stearate is normally within the range of 16.5 to 17. The HLB value of the polyoxyethylene sorbitan mono-oleate is normally 15. Accordingly, the average HLB value of the nonionic surfactant system of this invention is above 16. The glycol component was melted and maintained within the temperature range of 55°–70° C. during manufacture of the suppository composition. Manufacture was carried out on a batch basis, but can also be done continuously.

One part of antioxidant, BHT (butylated hydroxy toluene) was added to 10,000 parts of the composition described above. A suppository cast from this composition was 30 mm in length and 13 mm wide at its widest point. (Suppositories 10–50 mm in length and 2–20 mm in width can easily be cast and molded.)

Although not ordinarily preferred, medicaments related to coitus such as spermicides and bactericides may be added to suppository compositions of this invention.

Throughout this application, the terms "polyethylene glycol" and "polyoxyethylene glycol" are used synonymously.

What is claimed is:

1. A lubricating suppository for the human vaginal canal, which suppository is solid at normal ambient temperatures but melts at human body temperature to form a substantially homogeneous liquid having the appearance of a single liquid phase, said suppository comprising:
   (a) a continuous phase comprising a water soluble polyoxyalkylene polyol component consisting essentially of polyoxyethylene glycol having a molecular weight within the range of 400 to 5000, said component being formulated to have a melting range low enough to ensure the formation of a clear molten liquid at less than about 75° C.;
   (b) about 10–60 parts per one hundred parts by weight of said polyoxyalkylene polyol component, of a nonionic surfactant having an HLB value greater than 12, said nonionic surfactant being uniformly distributed through said continuous phase;
   (c) about 10–40 parts per hundred, based on the weight of said polyoxyalkylene polyol component, of a $C_6$–$C_{12}$ aliphatic carboxylic acid glyceride said glyceride being uniformly distributed throughout said continuous phase with the aid of said nonionic surfactant;
said lubricating suppository, in either the solid or molten state, having sufficient compatibility with water to be readily uniformly distributable in water.

2. A suppository according to claim 1 wherein said continuous phase further comprises a lower aliphatic monomeric hydrophilic polyol dissolved in said continuous phase.

3. A suppository according to claim 2 wherein said hydrophilic polyol is glycerin.

4. A suppository according to claim 1 wherein said nonionic surfactant comprises a blend of oxyethylene chain-containing esters or ethers, said blend having an HLB value above about 14, the ester or ether functional groups of said esters or ethers comprising a higher aliphatic residue.

5. A suppository according to claim 4 wherein said HLB value is less than about 18.

6. A suppository according to claim 1 consisting essentially of:
   (a) 50–70% by weight of a blend of polyoxyethylene glycols with a molecular weight within the range of about 900 to about 2000, which blend at least begins to melt at temperatures no higher than about 50° C.;
   (b) dispersed in said blend of polyoxyethylene glycols, 10–20% by weight of a triglyceride of at least one $C_6$–$C_{12}$ saturated aliphatic carboxylic acids;
   (c) dissolved in said blend of polyethylene glycols, 10–30% by weight of a blend of nonionic surfactants selected from the group consisting of poly(oxyethylene) polyol ethers, poly(oxyethylene) polyol ethers, and mixtures thereof, said blend having a weight-average HLB value of at least about 14; and
   (d) 0–20% by weight of glycerin dissolved in said blend of polyoxyethylene glycols.

7. A suppository according to claim 6 which further includes an effective amount of an antioxidant.

8. A solid, pre-coital, vaginal lubricant suppository which melts at 37° C., said suppository having been cast and solidified from a generally homogeneous molten mass comprising:
   a continuous phase consisting essentially of:
   (a) 50–70% by weight, based on the weight of the suppository, of a blend of glycols consisting essentially of:
      (1) a polyoxyethylene glycol having an average molecular weight of 900–1100, and
      (2) a polyoxyethylene glycol having an average molecular weight of 1200–1700, the ratio of glycol (2) to glycol (1) ranging from about 1:1 to about 4:1;
   (b) 5–20% by weight, based on the weight of the suppository, of glycerin;
   (c) 10–30% by weight, based on the weight of the suppository, of a combination of nonionic surfactants having a weighted-average HLB value of about 14 to about 18, said combination comprising polyoxyethylene lauryl ether and polyoxyethylene stearate; and
   (d) as a discontinuous phase emulsified in and distributed uniformly throughout said continuous phase, a triglyceride of coconut origin containing caprylic and capric acid residues.

9. A suppository according to claim 8 comprising:
   50% by weight of said glycol blend,
   20% by weight of said triglyceride,
   10% by weight of glycerin,
   10–15% by weight of a polyoxyethylene lauryl ether having an HLB value of about 16.5 to about 17,
   0–5% by weight of a polyoxyethylene sorbitan monooleate having an HLB value of about 15,
   5–10% by weight of a polyoxyethylene stearate having an HLB value of about 16.5 to about 17, and p1 an effective amount of an alkylated hydroxyaromatic antioxidant.

10. A method for pre-coitally lubricating the human vagina with a liquid lubricant comprising the step of:
    (a) inserting a solid suppository of claim 1 into the vagina, and
    (b) permitting said suppository to melt within the vagina prior to coitus to form a water-compatible, lubricitous liquid coital lubricant.

11. A method for making a lubricating suppository which is solid at room temperature but melts at human body temperature, comprising the following steps:
    (a) melting a blend of solid polyoxyethylene glycols at a temperature above normal ambient temperatures but below about 75° C., thereby obtaining a homogeneous melt;
    (b) dissolving in the melt about 10–60 parts by weight, per 100 parts by weight of said polyoxyethylene glycols, of nonionic surfactant having a HLB value above 12, while maintaining the melt at a temperature above normal ambient;
    (c) distributing throughout the melt produced by step (b) about 10–40 parts by weight, per 100 parts by weight of said polyoxyethylene glycols a solid glyceride of at least one $C_{6-12}$ aliphatic carboxylic acid, until said solid glyceride forms a discontinuous phase uniformly distributed through the melt produced by step (b) and emulsified in said melt, while maintaining the resulting emulsified, two-phase melt at a temperature above normal ambient; and
    (d) casting portions of the resulting two-phase melt into the form of suppositories and solidifying the thus-cast portions.

12. A lubricating suppository made according to the method of claim 11.

* * * * *